United States Patent [19]

Feldman et al.

[11] Patent Number: 4,824,238

[45] Date of Patent: Apr. 25, 1989

[54] COMPARATOR FOR OPTIC DISC ANALYSIS AND METHOD OF USE THEREOF

[75] Inventors: Robert L. Feldman, Philadelphia, Pa.; George L. Spaeth, 15 Laughlin La., Chestnut Hill, Pa. 19118

[73] Assignee: George L. Spaeth, Chestnut Hill, Pa.

[21] Appl. No.: 56,374

[22] Filed: May 27, 1987

[51] Int. Cl.⁴ .......................... A61B 3/02; A61B 3/14; G03B 29/00

[52] U.S. Cl. ................................ 351/206; 351/222; 351/237; 356/390

[58] Field of Search ............... 351/205, 222, 237, 246, 351/206, 207, 208; 356/390, 391, 392, 393; 354/62

[56] References Cited

U.S. PATENT DOCUMENTS

| | | | |
|---|---|---|---|
| 2,460,350 | 2/1949 | Hinman | 356/393 |
| 2,765,704 | 10/1956 | Mottu | 356/393 |
| 3,737,217 | 6/1973 | Haines | 351/237 X |
| 4,340,281 | 7/1982 | McIntyre | 351/205 |

Primary Examiner—Rodney B. Bovernick
Attorney, Agent, or Firm—Siegmar Silber

[57] ABSTRACT

A method is provided of comparing eye fundus slides for analysis. This method includes using an archival slide for a reference, preparing a current eye fundus slide and comparison with the reference and using a two-projector system for superimposing the image of the current eye fundus slide on the image of the reference.

7 Claims, 2 Drawing Sheets

COMPARATOR FOR OPTIC DISC ANALYSIS AND METHOD OF USE THEREOF

BACKGROUND OF THE INVENTION

1. Field of the Invention

This invention relates to optic disc analysis which technic is a useful aid in glaucoma detection. More specifically, a comparator apparatus and diagnosis is described by which two eye fundus photographic slides are superimposed so that blood vessel changes over substantial periods of time are monitored. Evaluation of these photographic slides is of particular importance as there is a large and significant collection of monoscopic eye fundus slides.

2. Disclosure Information Statement

In preparation for this application several searches were conducted. These included a computerized search of a medical literature database (MEDLINE), a computerized search of a patent database (DERWENT), and a manual pre-examination patentability search. These various searches did not uncover any highly relevant references. The manual search entailed a review of the following classes and subclasses:

| Class | Subclasses |
| --- | --- |
| 351 | 7 and 206 |
| 354 | 62 |
| 128 | 745, 665, 666 and 667 |

The search uncovered the following patents:

| U.S. Pat. No. | Inventor | Date of Issue |
| --- | --- | --- |
| 4,249,825 Of Interest Only | Shapiro | 2/10/81 |
| 4,402,325 | Sawa | 9/6/83 |
| 4,166,695 | Hill et al | 9/4/79 |
| 3,804,529 | Kilmer et al | 4/16/74 |
| 3,478,658 | Yow Jiun Hu et al | 11/18/69 |
| 2,573,464 | Lowenstein et al | 10/30/51 |

In U.S. Pat. No. 4,249,825, Shapiro discloses a photographic-based system which looks at blood vessel image changes in time where use of special dyes are inherent as is the rapid time sequence.

No patent was found dealing with a long time period recording and comparison of fundus blood vessel images, or with any dual projector dual filter apparatus. Other patents found and listed above were considered merely of interest.

In opthamology, the practice of obtaining photographic slides of the eye fundus region is in general use to monitor optic disc deterioration. In glaucoma, this deterioration is evidenced by optic atrophy with glaucomatous cupping. It has long been felt that, utilizing existing patient archival material for displacement of optic dis vasculature, would be highly desirable. Until the apparatus and method of the present invention, no simple comparator other than visual side-by-side comparisons of slides, was available for use with the patient archival material.

SUMMARY OF THE INVENTION

In the disclosure an apparatus is described which is analyzing optoc disc changes in monoscopic optic disc slides. Such slides have been developed over the years by periodic photography with a mydriatic-type eye fundus camera. In some diseases of the eye, especially glaucoma, diagnosis is gained by detection of optic disc deterioration. The eye fundus includes a cup-like portion, and extending over the interior surface thereof are a plurality of blood vessels. With the deterioration of the optic disc, these vessels undergo corresponding shifts in position. However, because the conditions under which the eye is photographed also change, the monoscopic slides are frequently difficult to analyze.

To simplify analysis, a device, a which consists of two slide projectors at 90° angles to one another, an image splitter, a mirror and a viewing screen, is provided. Compensation for changed photographic conditions is accomplished in part by zoom lenses and adjustable projector stages. Each pair of projected images from monoscopic slides are superimposed by reflecting one image onto the same projection pathway as the other. The combined image is then reflected by mirror onto a ground glass viewing screen and is observed from the opposite side. Changes are seen as areas where images do not superimpose. Enhancement of differences between the slides is achieved by placing a blue filter in front of one projector and a neutral density filter in front of the other. Further clarification of differences can be achieved rapidly switching on and off one of the projectors. In testing for accuracy, 28 eyes of 15 patients, who had optic disc photographs at least 10 years apart were studied, without filter enhancement for positional changes in optic disc vasculature. The images, once aligned in general, are compared as areas of blood vessels which do not superimpose, may be indicative of worsening glaucoma.

Accordingly, it is an object of the present invention to provide a comparator for optic disc analysis which, by showing changes in the blood vessels of the optic dics, aids in glaucoma detection and diagnosis.

It is a further object of the invention to compare photographic slides from mydriatic-type eye fundus cameras to detect deterioration of the optic disc vasculature.

It is a yet further object of the invention to utilize the vast collection of eye fundus photographic slides, presently extant, in the detection and diagnosis of glaucoma.

It is a feature of the present invention to use zoom lenses and mechanical projection stages to align superimposed images of eye fundus slides, and, specifically, the optic disc portions of the slides.

It is another feature of the present invention to utilize filters and intermitten projection technics to differentiate optic disc vasculature of superimposed images.

Other objects and features of the invention will become apparent as the drawings which follow are understood by reading the corresponding description thereof.

DESCRIPTION OF THE PREFERRED EMBODIMENTS

As noted previously, the examination of the ocular fundus in glaucoma is directed particularly to deriving evidence of deterioration of the optic disc and the shift in the vasculature thereof, particularly branches of the central retinal artery. Other vasculature movement may be seen by observing the small branches of the vascular circle of the optic nerve, which are branched mainly from the posterior ciliary arteries. Further, it appears that the superior and inferior temporal nerve fibers of the optic disc are most vulnerable to increased intraocular pressure and that the initial disc changes in glaucoma may occur there. Vaughn in his text notes that optic disc changes are the most important early findings of glaucoma. Further as time elapses, the temporal disc margin thins, the cup-shaped area excavates and becomes wider and deeper. The larger vessels of the disc vasculature are circumferentially displaced. To facilitate the aforesaid examination, an apparatus or comparator for optic disc analysis is shown herein and the method of use thereof is explained.

Figure 1:
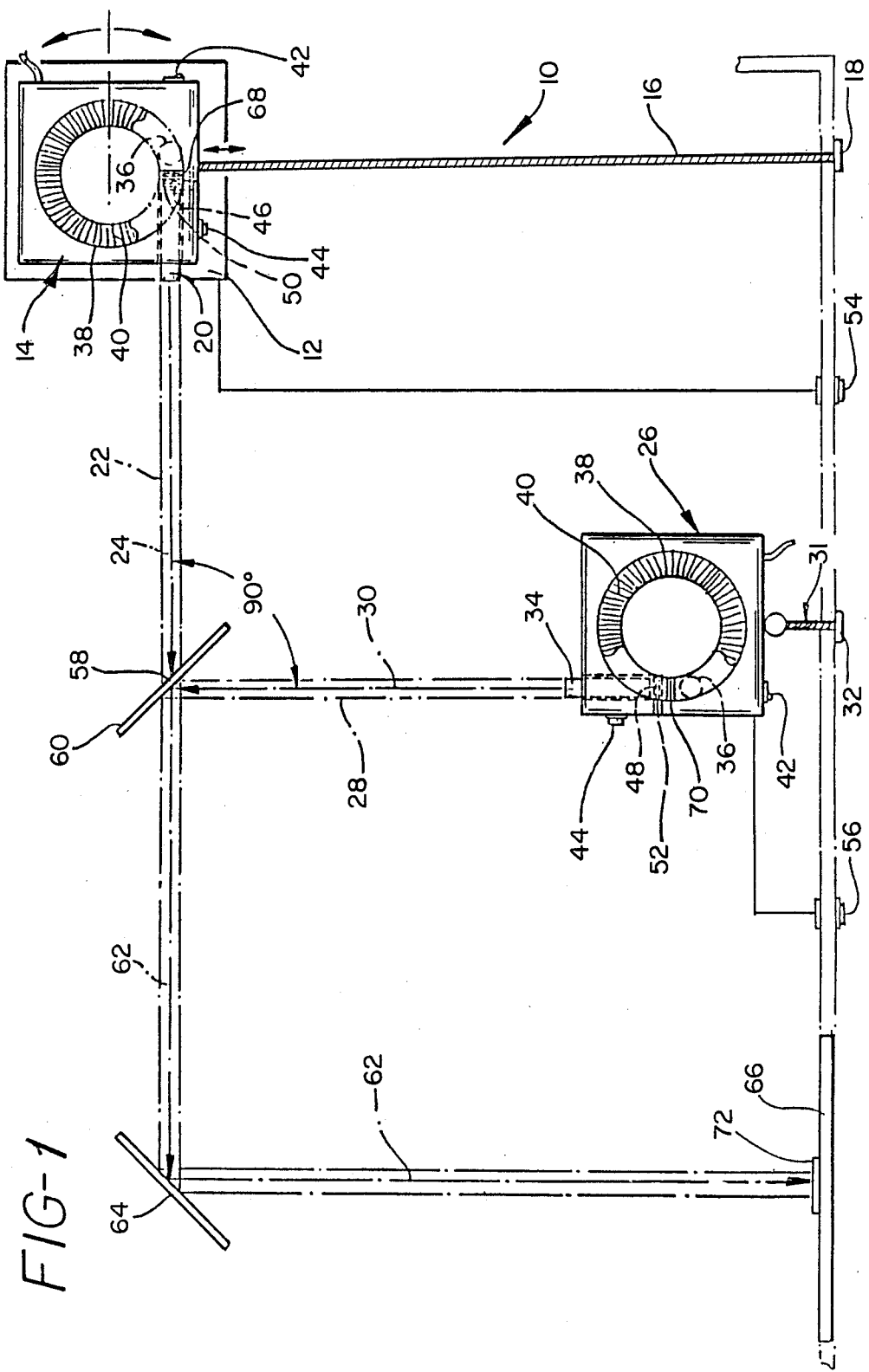
FIG. 1 is a schematic view of the optic disc analysis apparatus of the present invention, and, FIG. 2 is a view of two eye fundus images one superimposed upon the other.
Figure 2:
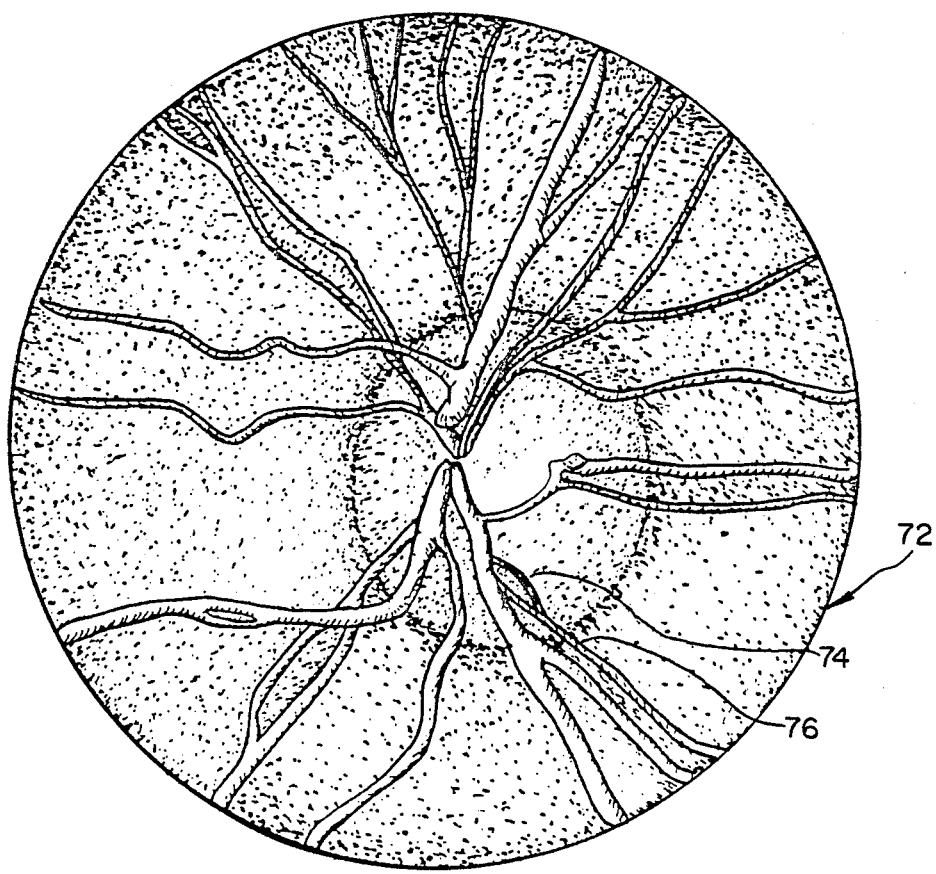

Referring now to FIG. 1, the comparator apparatus on optic disc analysis device is shown and is generally referred to by the numeral 10. A projector stage 12 is constructed to provide adjustable mounting on two axes for a slide projector 14. In the discussion which follows, commercially available optical/photographic components are utilized in the two-projector comparator 10; however, it is understood that a dual-slide projector with a single lamp and special slide carrier can be constructed for the within purpose, such a device would not depart from the spirit hereof and would be within the scope of one skilled in the art. The projector stage 12 is further constructed to include a fine horizontal adjustment 16 and associated to control knob 18 for enhancing the superimposition of the eye fundus slides. For similar purpose, a zoom lens 20 is included in the projector 14. The projector 14 established a projection pathway 22 having, in turn, longitudinal axis 24. For comparison purposes, a second projector 26 is mounted in the apparatus 10. This projector 26 is aligned so that the second projection pathway 28 thereof having, in turn, a second longitudinal axis 30 is substantially at right angles to and coplanar with the first longitudinal axis 24. The second projector 26, for ease of calibration with the first projector 14 is constructed to include a fine vertical adjustment 31 and associated control knob 32. Like the first projector 14, the second projector 26 also is equipped with a zoom lens 34. For operations, both projectors are constructed with a projector lamps 36, slide cartridge 38, slide inserter 40, ON/OFF switch 42, and zoom control 44. The first projector 14 and second projector 26 incorporate for differentiation purposes, filter housings 46 and 48 and associated filters 50 and 52, respectively. The first projector 14 and second projector 26 optionally incorporate for differentiation purposes intermittent operation switches 54 and 56, respectively. At the juncture 58 of the two projection pathways 22 and 28 (or more accurately of their longitudinal axes 24 and 30), a beam splitter 60 is arrayed for merging the pathways onto a common projection pathway 62. For convenience, a surface mirror 64 is optionally provided which, in turn, projects the images onto a ground glass, back-projected viewing screen 66.

In operation, the apparatus 10 is first calibrated so that the alignment of axes 24 and 30 are coplanar using levelling means and height (vertical) adjustment 31 and secondly calibrated so that the alignment of axes 24 and 30 are substantially at 90° the one to the other and in any event, properly incident upon beam splitter 60. With the equipment calibrated, an archival eye fundus slide 68 is placed in slide cartridge 38 and a current eye fundus slide 70 is placed in the other slide cartridge 38. The slides are then sequentially presented for projection and zoom lenses 44 area adjusted to enhance superimposition of one slide upon the other. Where, for example, the film is mounted slightly differently in the slide frames, fine adjust horizontal control 16 and fine adjust vertical control 31 are employed to compensate therefor. With the superimposition of images from slides 68 and 70, the changes with time of the optic disc and the vasculature surrounding the cup-like structure are next examined. Colored filter 50—a blue filter—is placed in the projection pathway of slide 68 and colored filter 52—a neutral density filter—is placed in the projection pathway of slide 70. With the differential thus provided, vascular shifts (as in the textbook example of being circumferentially displaced) can be clearly and conveniently observed and, further, can be monitored with respect to time elapsed.

The method of comparing eye fundus slides for analysis thereof to determine optic disc deterioration (cupping) and to monitor displacement of optic disc vasculature is next described. From the prior discussion, such analysis is seen to utilize a comparator 10 for superimposing the projected images from two slides 68 and 70 along a given single common pathway. Initially to distinguish between instrumentation and medical protocols in the discussion of the method of comparison, the step set forth is with a comparator 10 that is fully calibrated. Later, the steps of the method of analysis are expanded to include the calibration. The method of comparison include the steps of:

a. retrieving an archival eye fundus slide for use as a reference;
b. projecting the image of the reference along a given first pathway;
c. preparing a current eye fundus slide for comparison with the reference;
d. projecting the image of said current eye fundus slide along a given second pathway;
e. superimposing the image of the current eye fundus slide on the image of the reference by the substeps of:
   1. optically merging said first and said second projection pathways into a resultant common projection pathway;
   2. adjusting the respective images until the outlines thereof are substantially coincident; and,
   3. viewing the superimposed image 72 of the current eye fundus slide on the reference;
f. differentiating the current eye fundus 74 structure from the reference structure 76; and,
g. visually analyzing changes with respect to time of optic disc conditions.

From the above steps, it is clear that slight variations in mydriatic-type eye fundus photography are compensated by the step e.1, adjusting. With the apparatus described hereinabove, this step is accomplished using fine adjust horizontal and vertical controls for optical axes alignment (concentricity) and the zoom lenses for the sizing of the images. Differentiation of the structures is gained in two ways, namely, the intermittent operation of one of the slide projectors and by coloring one or both of the projected images. The visual analysis, step g, above, includes observing OPTIC disc cupping—change in outline of the optic disc—and observing vascular shifts—optic disc—and observing vascular shifts—displacement of the vessels from the archival eye fundus slide position to the one shown in the current eye fundus slide position.

The method further includes the instrument calibration steps of:
a. optically aligning the longitudinal axis of the first projector to be coplanar with the longitudinal axis of the second projector; and,
b. adjusting the mounting of the first projector until the first projection pathway is substantially at a 90° angle with the second projection pathway.

Obviously calibration procedures vary considerably from one instrumentation arrangement to another. Coplanarity is aided by levelling of both projections and height adjustment of one projector. Similarly, rectangularity is aided by the adjustable projector stage, and, with one projector fixed, the x-axis and y-axis settings of the other projector ensures "squaring of the apparatus."

Although the best mode of the invention has been described herein in some detail, it has not been possible to include each and every variation. Those skilled in the art of diagnosing worsening glaucoma will be able to make slight variations in the mechanical arrangement suggested hereby without departing from the spirit of the invention and still be within the scope of the claims appended hereto.

What is claimed is:

1. A method of comparing eye fundus slides for analysis thereof comprising the steps of:
   a. retrieving an archival eye fundus slide for use as a reference;
   b. using an adjustably mounted first projector, projecting the image of the reference along a given first pathway;
   c. preparing a current eye fundus slide for comparison with the reference;
   d. using an adjustably mounted second projector, projecting the image of said current eye fundus slide along a given second pathway;
   e. superimposing the image of the current eye fundus slide on the image of the reference by the substeps of:
      1. optically merging said first and said second projection pathways into a resultant common projection pathway;
      2. adjusting said first and said second projector until the outlines of the respective eye fundus images thereof are substantially coincident; and,
      3. viewing the superimposed image of the current eye fundus slide on the reference;
   f. differentiating the current eye fundus structure from the reference structure; and,
   g. visually analyzing changes with respect to time of optic disc conditions.

2. A method as described in claim 2 wherein the step of adjusting the respective images further includes the vertical adjustment of one of said projectors and the horizontal adjustment of one of said projections.

3. A method as described in claim 2 wherein the step of adjusting further includes operating a zoom lens on each projector to enlarge and reduce the size of the projected images.

4. A method as described in claim 1 wherein said step of differentiating includes the inserting of a filter in one of the projection pathways whereby, upon insertion thereof, said respective filter eye fundus image is differentiated from the other eye fundus image.

5. A method as described in claim 1 wherein said step of differentiating includes alternately removing from and inserting into the superimposed image one of said eye fundus images in a predetermined time sequence.

6. A method as described in claim 1 further including the step of optically aligning the longitudinal axis of the first projector to be coplanar with the longitudinal axis of the second projection.

7. A method as described in claim 1 further including the step of adjusting the mounting of the first projector until the first projection pathway is at a 90° angle with the second projection pathway.

* * * * *